United States Patent [19]

Green

[11] Patent Number: 4,776,506

[45] Date of Patent: Oct. 11, 1988

[54] SURGICAL STAPLER APPARATUS

[75] Inventor: David T. Green, Norwalk, Conn.

[73] Assignee: United States Surgical Corporation, Norwalk, Conn.

[21] Appl. No.: 930,662

[22] Filed: Nov. 13, 1986

[51] Int. Cl.⁴ .............................................. A61B 17/00
[52] U.S. Cl. ................................. 227/19; 227/DIG. 1
[58] Field of Search ............... 128/334 R, 334 C, 335; 227/19, DIG. 1, 8, 141

[56] References Cited

U.S. PATENT DOCUMENTS 4,671,445  6/1987  Barker et al. ...................... 227/141

Primary Examiner—Paul A. Bell

Attorney, Agent, or Firm—Kenyon & Kenyon

[57] ABSTRACT

The end-to-end anastomosis surgical stapling apparatus is actuated in a single step. The apparatus includes a shaft which is able to pull the stapling anvil proximally in one step relative to a stationary housing as well as a plurality of circumferentially disposed balls mounted in cage-like manner in the housing which serve to lock the sleeve relative to the housing. The sleeve carries the staple cartridge and is released to move with the anvil when the anvil clamps the tissue against the cartridge. Thereafter, cam surfaces on the shaft and the sleeve permit the balls to move radially inwardly releasing the sleeve for proximal movement relative to the housing so that the staples pierce the tissue for stapling purposes.

29 Claims, 3 Drawing Sheets

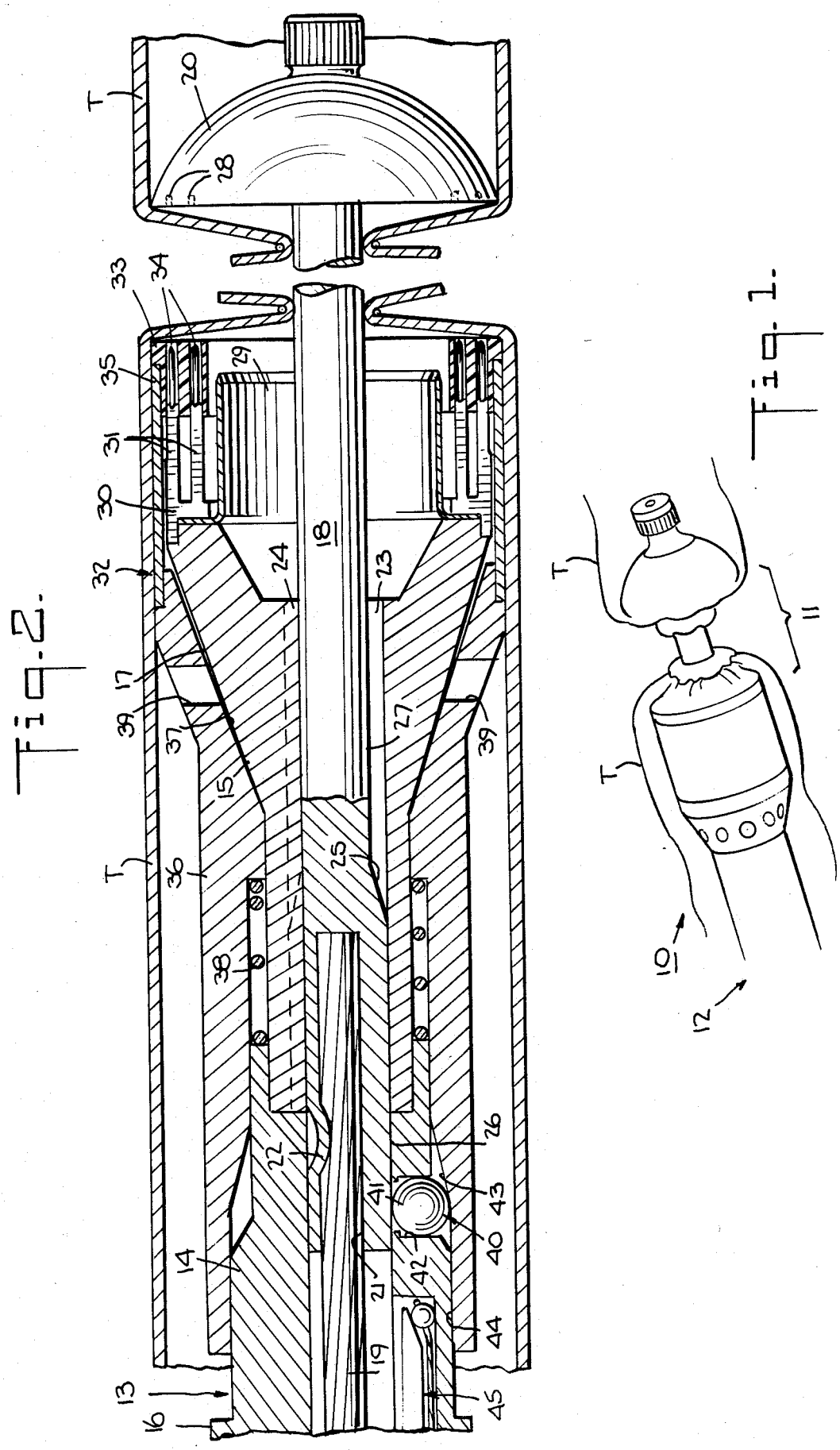

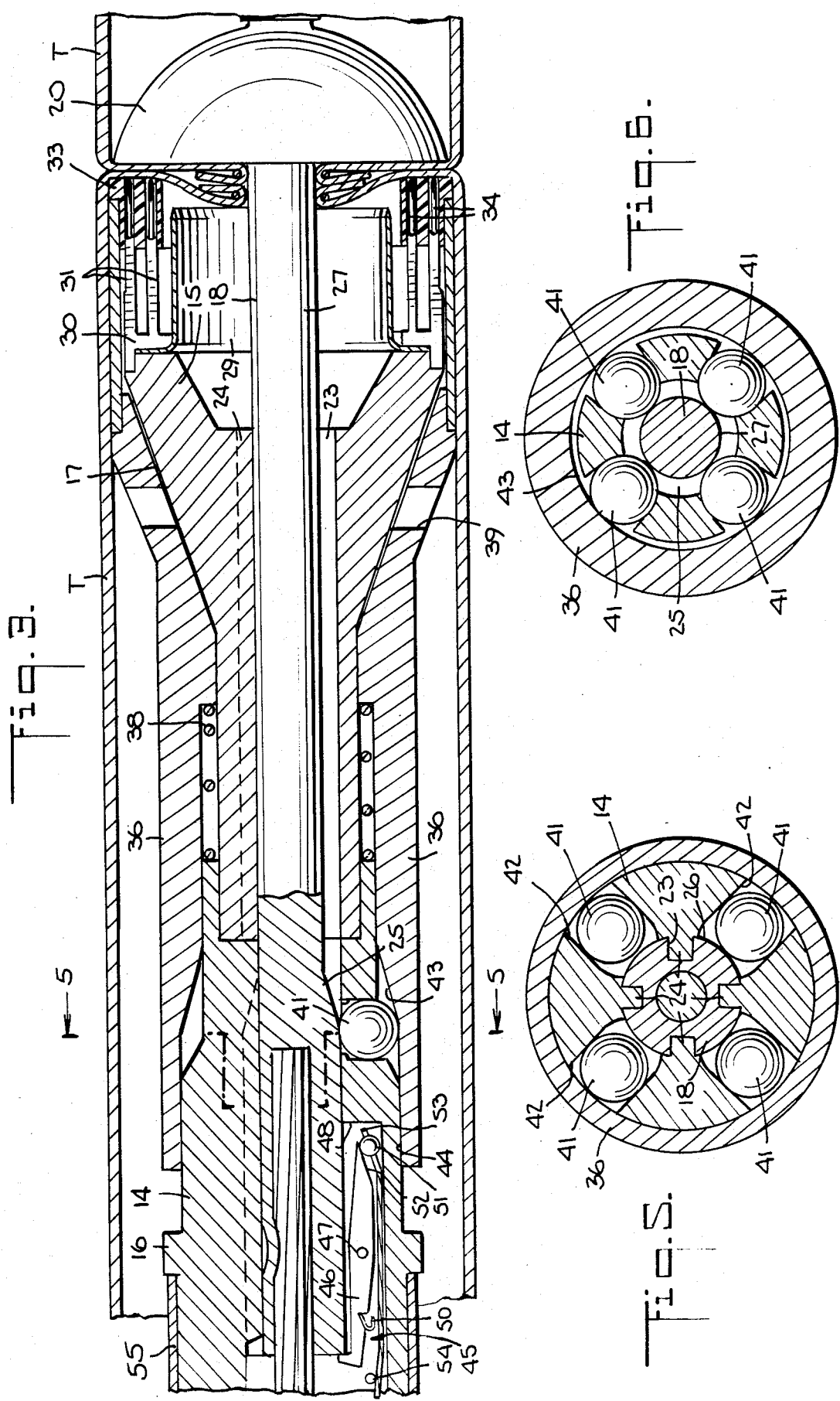

SURGICAL STAPLER APPARATUS

This invention relates to a surgical stapler apparatus. More particularly, this invention relates to a flexible surgical stapler apparatus for use in end-to-end anastomosis.

As is known, various types of surgical stapling devices have been used for the stapling of tissue. In particular, various types of devices have been known for an end-to-end anastomosis for rejoining the lumen of a tubular organ. In such cases, the devices have been provided with a stationary anvil against which staples may be formed by applying a force through staple pushers which serve to eject the staples from a cartridge against the anvil. In addition, these devices have also employed a flexible shaft, for example, as described in U.S. Pat. Nos. 4,485,817 and 4,488,523 for the stapling of sites which may be inaccessible for devices having a rigid shaft.

European Patent Application No. 0173451, published Mar. 5, 1986 describes a flexible stapler assembly having an anvil which is movable against stationary staples. As described, a staple pusher is mounted in a stationary manner on a firing head assembly while a cable is secured to the anvil for pulling of the anvil relative to the stationary staple pusher in order to drive the staples through the tissue to be stapled. However, the described assembly requires a number of springs which, in turn, complicate the construction as well as the operation of the assembly.

Accordingly, it is an object of the invention to provide a surgical stapler apparatus of relatively simple construction having a movable anvil.

It is another object of the invention to simplify the construction of a flexible stapler apparatus employing a movable anvil.

Briefly, the invention provides a surgical stapler apparatus, for example of the flexible end-to-end anastomosis type, which employs a housing and a shaft which is movably mounted in the housing for relative longitudinal movement. In addition, an anvil is mounted on a distal end of the shaft, an annular knife projects axially from the distal end of the housing towards the anvil and an annular stapler pusher projects axially from the distal end of the housing towards the anvil radially outside the knife. Likewise, a suitable means, such as a cable is provided for moving the shaft into the housing and, thus, the anvil towards the knife.

In accordance with the invention, an annular means is provided for mounting an annular stapling cartridge having a plurality of staples on the housing in alignment with the pusher. This means includes a sleeve which is slidably mounted on the housing for the movement between an extended position corresponding to a retained position of the staples in the cartridge and a retracted position corresponding to an expelled position of the staples from the cartridge. This means also includes a mounting ring which is secured to and which extends from the sleeve concentrically about the pusher and the knife for mounting of a stapling cartridge therein.

In addition, cam means are provided for securing the sleeve relative to the housing during movement of the shaft and anvil to a predetermined point spaced from the knife so as to prevent movement of the sleeve and thus the cartridge. Further, a cam surface is provided on the shaft at an intermediate location within the housing in order to actuate the cam means and, thus, release the sleeve for movement relative to the housing in response to continued movement of the shaft and, thus, the anvil towards the knife. In this way, the anvil pushes the cartridge relative to the pusher in order to expel the staples of the tissue between the anvil and the cartridge.

The cam means may be in the form of a plurality of circumferentially spaced balls which are mounted in the housing for radial movement during passage of the cam surface of the shaft thereby. In this case, the cam surface may be a conical annular surface located between an enlarged diameter portion of the shaft and a smaller diameter portion of the shaft.

The housing is formed of a pair of coaxial sections which are telescopically fitted into each other with a spring between one of the housing sections and the sleeve for biasing the sleeve into the extended position. The other housing section includes a conical exterior surface while the sleeve has a conical interior surface for abutting the exterior surface of the housing section when in the extended position. The formation of the housing into two sections facilitates the assembly of the sleeve over the housing.

The shaft is disposed within the housing in a non-rotatable manner. To this end, for example, the shaft is provided with at least one longitudinal spline while the housing is provided with at least one groove receiving the spline in order to secure the shaft against rotation in the housing.

In addition, a releasable lock means is provided for preventing proximal movement of the shaft past a certain point in order to prevent premature firing of the staples.

In order to use the surgical stapler apparatus, the apparatus is positioned in the usual fashion relative to two sections of lumen which are to be joined together. After necking down of the two sections between the anvil and the cartridge, the shaft is drawn into the housing so that the anvil moves into a position in which the two sections of tissue are clamped between the anvil and the cartridge. At this time, the anvil is spaced and locked at a predetermined point from the knife, i.e. a tissue gap set position, and the cartridge is positively secured against axial movement. Thereafter, the lock means is actuated to release the shaft on which the anvil is mounted and the apparatus is actuated so that the anvil is pulled further towards the housing. The cam surface on the shaft then passes the cam means to release the sleeve and the anvil, by pressing the tissue against the cartridge, forces the cartridge to move over the pusher. The stationary staples then pierce the tissue between the cartridge and anvil. When the anvil has been brought to a stop, the ends of the staples will have passed through the tissue and will have been clinched by the anvil to secure the two sections of tissue together. At the same time, the annular knife will have cut through the the tissue in the usual manner.

After stapling, the anvil can be moved away from the housing via the cable and, thereafter, the instrument can be removed in the usual fashion.

These and other objects and advantages of the invention will become more apparent from the following detailed description taken in conjunction with the accompanying drawings wherein:

FIG. 1 illustrates a perspective view of the end of a surgical stapler apparatus constructed in accordance with the invention;

FIG. 2 illustrates a longitudinal sectional view of the surgical stapler apparatus of FIG. 1;

FIG. 3 illustrates a view similar to FIG. 2 with the anvil of the apparatus in a tissue gap set position spaced from an annular knife in accordance with the invention;

FIG. 5 illustrates a cross sectional view taken on line V—V of FIG. 3; and

FIG. 6 illustrates a view taken on line VI—VI of FIG. 4.

Figure 4:
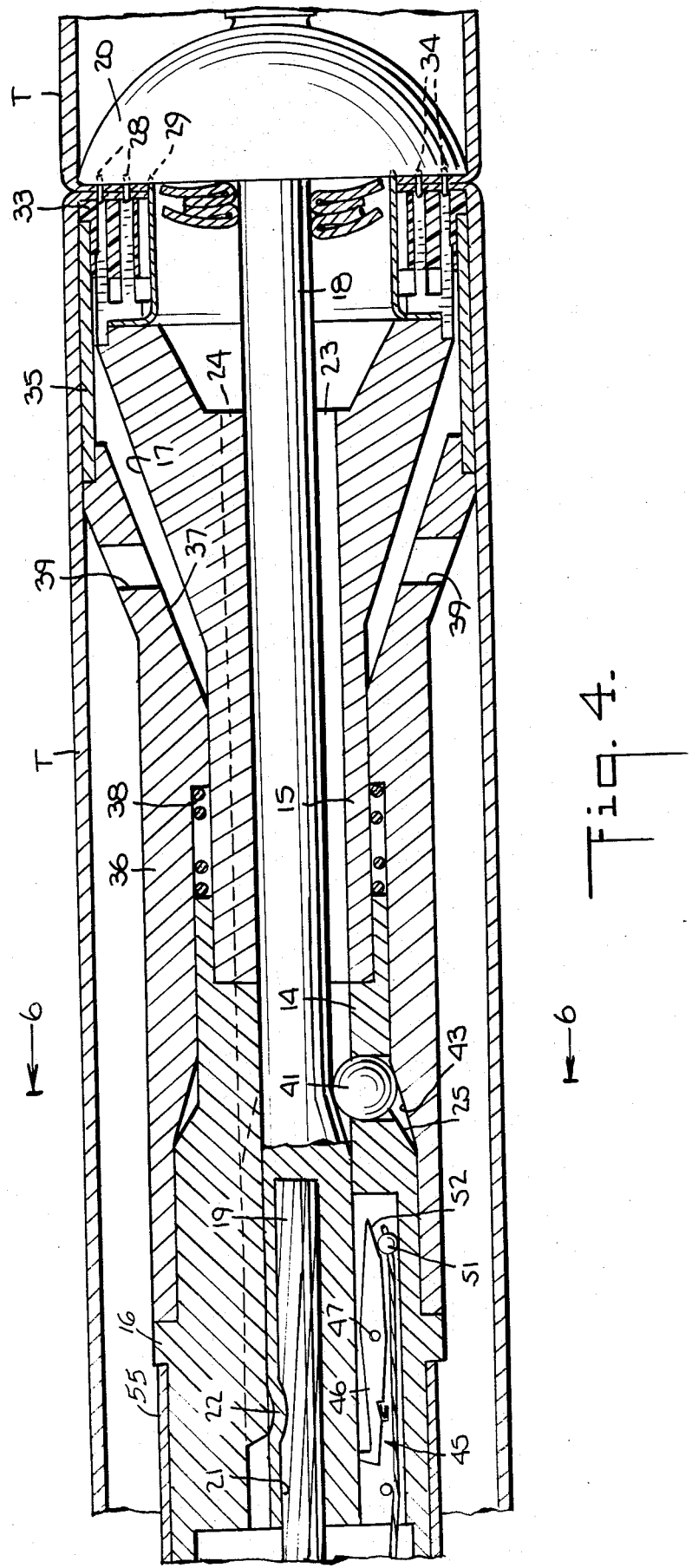
FIG. 4 illustrates a view similar to FIGS. 2 and 3 with the anvil in a fully retracted position in accordance with the invention.

Referring to FIG. 1, the surgical stapler apparatus 10 is of flexible construction. In this regard, the apparatus includes an applicator portion 11 at the distal end, an actuator portion (not shown) at a proximal end and a flexible shaft 12 joining the applicator portion 11 and the actuator portion (not shown). As indicated, the apparatus is used to staple together two sections T of tissue of a lumen.

Referring to FIG. 2, the applicator portion 11 includes a housing 13 which is formed of a pair of coaxial sections 14, 15 which are telescopically fitted into each other. The proximal housing section 14 includes an annular shoulder 16 near the proximal end for purposes as described below while the distal housing section 15 has an enlarged distal section which includes a conical exterior surface 17.

The applicator portion 11 also has a shaft 18 which passes through the housing 13 and is secured at the proximal end to a means such as a flexible cable 19, which extends to the actuator portion (not shown) and forms a part of the flexible shaft 12 for moving the shaft 18 relative to the housing 13. In addition, the distal end of the shaft 18 carries an anvil 20 which is removably mounted thereon by suitable means (not shown). As indicated in FIG. 2, the shaft 18 carries a central bore 21 in which the cable 19 is received as well as a clinched portion 22 by which the shaft 18 is fixed to the cable 19 in a permanent manner.

The shaft 18 is mounted in the housing 13 in a non-rotatable longitudinally movable manner. To this end, as indicated in FIGS. 2 and 5, the shaft 18 has a plurality of circumferentially spaced axially disposed grooves 23 while each housing section 14, 15 has a plurality of splines 24 which are slidably disposed in the grooves 23 in mating relation. The shaft 18 also has a conical annular surface 25 at an intermediate region within the distal housing portion 15 to separate an enlarged diameter portion 26 from a reduced diameter portion 27.

The anvil 20 is of conventional structure and includes, for example, two annular rows of indentations 28 for the clinching of staples.

As shown in FIG. 2, an annular knife 29 is mounted on the distal end of the housing 13 and projects axially therefrom towards the anvil 20. In addition, an annular staple pusher 30 is also mounted at the distal end of the housing 13 to project towards the anvil 20 radially outside the knife 29. This pusher 30 has two annular arrays of fingers 31 which project axially towards the anvil 20 Both the knife 29 and the pusher 30 are mounted on the distal end of the housing portion 15 in any suitable manner, for example in slide-fit non-rotatable relation.

An annular means 32 is also disposed about the distal end of the housing 13 in order to mount an annular stapling cartridge 33 containing, for example, two annular rows of staples 34 in alignment with the pusher fingers 31. This annular means 32 includes a mounting ring 35 and a sleeve 36.

The mounting ring 35 encircles the distal end of the housing 13 and covers over the pusher 30 and knife 29. In addition, the cartridge 33 is stepped, as shown, at the distal end so as to be fitted within the ring 35 while forming a smooth continuation of the outer surface of the ring 35.

The sleeve 36 has the ring 35 slidably mounted thereon in suitable fashion. In addition, the sleeve 36 is contoured to slidably fit over the two housing sections 14, 15 and has an internal conical surface 37 facing the external conical surface 17 of the distal housing section 15. When in the position illustrated in FIG. 2, the conical surfaces 37, 17 abut each other.

As shown in FIG. 2, a spring, such as a compression spring 38, is disposed between the end of the proximal housing section 14 and the sleeve 36 in order to bias the sleeve 36 in a distal direction. Further, the sleeve 36 is provided with a plurality of radial ports 39 which serve to vent the space between the sleeve 36 and the distal housing section 15.

Referring to FIG. 2, a cam means 40 is provided for securing the sleeve 36 relative to the housing 13 during movement of the anvil 20 to a predetermined point (see FIG. 3) spaced from the knife 29. The cam means 40 cooperates with the conical annular surface 25 of the shaft 18 which, thus, acts as a cam surface, and is positioned relative to the sleeve 36 for movement relative to the housing 13 in response to continued movement of the anvil 20 towards the knife 29 (see FIG. 4) whereby the anvil 20 is able to push the cartridge 33, mounting ring 35 and sleeve 36 relative to the pusher 30 in order to expel the staples 34 from the cartridge 34. As illustrated, the cam means 40 includes a plurality of circumferentially spaced latches in the form of balls 41 which are mounted in radial bores 42 in the proximal housing section 11 in a cage-like manner for radial movement during passage of the annular cam surface 25 thereby. In addition, the cam means 40 includes an inclined cam surface 43 on the sleeve 36 and a cylindrical surface 44 which extends proximally from the cam surface 43. As indicated in FIG. 2 which represents the extended position of the sleeve 36 and mounting ring 35, the balls 41 are positioned between and are in contact with the enlarged diameter portion 26 of the shaft 18 and the cam surface 43 of the sleeve 36 at the point where the cylindrical surface 44 merges into the cam surface 43. In this position, the shaft 18 can be moved in a distal or proximal direction relative to the housing 13 so that the balls 41 merely ride on the enlarged diameter portion 26 of the shaft 18. However the sleeve 36 is prevented from moving in a proximal direction relative to the housing 13 since the balls 41 otherwise jam the sleeve 36 against such a movement.

Referring to FIG. 3, when the shaft 18 is moved in the proximal direction relative to the housing 13, the cam surface 25 of the shaft 18 is brought into a position to permit the balls 41 to begin to move radially inwardly. Thereafter, if the shaft 18 and the sleeve 36 move proximally relative to the housing 13, the balls 41 are able to move radially inwardly by riding along the "inner" cam surface 25 and the "outer" cam surface 43 (see FIG. 4 and FIG. 6). Thus, the position illustrated in FIG. 3 indicates a position in which the sleeve 36 is released for axial proximal movement relative to the housing 13.

Referring to FIG. 3, in order to prevent inadvertant proximal movement of the sleeve 36 and, thus, a premature firing of the staples 34, a releaseable lock means 45 is provided to prevent proximal movement of the shaft 18 past a certain point. As shown, the lock means 45 includes a latch 46 which is pivotally mounted on a fixed pivot pin 47 within a suitable recess 48 in the proximal housing section 14. This latch 46 has a hooked end 49 which is sized to abut the proximal end of the shaft 18 when the shaft 18 moves proximally, e.g. from the position shown in FIG. 1 to the position shown in FIG. 3. A spring 50 is also provided to bias the latch 46 into the locking position shown.

In order to release the latch 45, a cam means 51 in the form of a ball engages between an inclined cam surface 52 at a distal end of the latch 45 and a wall of the recess 48. In addition, a cable 53 passes through the ball 51 in fixed relation and extends over a guide pin 54 in the recess 48 and through the flexible shaft 12 to a point e.g. at a proximal end of the applicator portion 11. The proximal end of the cable 53 is mounted in a manner to be pulled by a surgeon in order to release the latch 45. In this regard, pulling of the cable 53 causes the ball 51 to move proximally which, in turn, pivots the latch 45 counter-clockwise, as viewed, from the locking position to a release position with the hooked end 49 out of the path of the shaft 18.

Referring to FIG. 4, the flexible shaft 12 includes a flexible axially rigid tube 55 of conventional construction which extends from the actuator portion (not shown) about the cable 19 to the housing 13 of the applicator portion 11. As indicated, the tube 55 abuts against the annular shoulder 16 of the proximal housing section 14 so as to retain the housing 13 in a stationary manner relative to the actuator portion (not shown). Other suitable means (not shown) may also be provided in abutment with the proximal end of the housing 13 in order to maintain the housing 13 stationary relative to the applicator portion 11.

As indicated in FIG. 2, the applicator portion 11 is in an open position. As this time, the sleeve 36 is in an extended position and the staples 34 are in a retained position within the cartridge. In additio, the shaft 18 is free to move axially while the balls 41 lock the sleeve 36 relative to the housing 13.

In operation, the surgical stapler apparatus 10 is inserted into the lumen of two tissue sections T which are to be drawn together. After necking down of the two sections T between the anvil 20 and the cartridge 33 as shown in the open position of FIG. 2, the shaft 18 is drawn into the housing 13 by pulling on the cable 19 via suitable linkages in the actuator portion (not shown) as is known. This movement proceeds with the anvil 20 moving into a predetermined position spaced from the cartridge 33, for example by a distance of 1 to 1.5 millimeters. In this tissue gap set position, as shown in FIG. 3, the two sections of tissue T are clamped between the anvil 20 and the cartridge 33. In addition, the shaft 13 abuts against the hooked end 49 of the spring biased latch 45 and is locked against further proximal movement together with the sleeve 36.

Next, the surgeon pulls on the proximal end of the cable 53 to pivot the latch 46 and, thus, release the shaft 18 for further movement.

Thereafter, the surgeon actuates the apparatus 10, for example by triggering a pistol grip or handle (not shown) in the actuator position 11 which is linked to the cable 19 in a suitable manner (not shown) in order to pull the cable 19 and, thus, the shaft 18 proximately a short distance. In this way, as the shaft 18 is thus pulled in the proximal direction, the anvil 20 is pulled towards the housing 13. At this time, the anvil 20 presses the clamped tissue T against the cartridge 33 and, thus, forces the cartridge 33 to move over the pusher 30. Also, at this time, the balls 41 begin to move radially inwardly under the camming action of the cam surface 43 of the sleeve 36 against the bias of the spring 38. Continued motion causes the stationary staples 34 to pierce the tissue T. As indicated in the fired position of FIG. 4, when the anvil 20 has been brought to a stop, the ends of the staples 34 will have passed through the tissue T and will have been clinched via the indentations 28 on the anvil 20 so as to secure the two sections of tissue T together.

During the stapling action, the annular knife 29 cuts the inner circumferential edges of the tissue T in the usual fashion.

After stapling, the applicator portion (not shown) is actuated in a conventional manner to move the shaft 18 and anvil 20 distally so as to unclamp the stapled tissue joint and thereafter the stapler apparatus 10 is removed form the lumen.

The cam means 40 for preventing movement of the cartridge 33 relative to the staples 34 until stapling action is required is of relatively simple reliable construction. In this respect, the position (i.e. tissue gap) at which the anvil 20 is initially brought into a predetermined spaced position from the staple cartridge 33 can be easily and precisely determined by the construction of the various components of the applicator portion 11.

The spring 38 may be of any suitable strength so as to initially bias the sleeve 36 against the conical exterior surface 17 of the housing section 15 while at the same time being of a weak strength to permit the anvil 20 to move the cartridge 33 proximally via the clamped tissue T. That is, the strength of the spring 38 should not be such that the anvil 20 would crush the tissue T.

Of note, when the anvil 20 is moved away from the stapled tissue, the cam surface 25 on the shaft 18 begins to bias the balls 41 radially outwardly. Thus, the balls 41, in turn, serve to push to sleeve 36 distally relative to the housing 13 along with the biasing force produced by the spring 38. In addition, as the anvil 20 is moved distally, the latch 45 is spring biased back into the locking position behind the shaft 18.

The surgical stapling apparatus 10 is preferably actuated in a single step manner as described above but may also, be constructed so that the anvil 20 moves in two stages from the open position shown in FIG. 2 to the tissue gap set position shown in FIG. 3 and then to the fired position shown in FIG. 4.

The invention thus provides a flexible surgical stapler apparatus wherein an anvil can be moved relative to a stapling cartridge in a relatively simple easy-to-use and reliable manner.

Further, the invention provides an end-to-end anastomosis stapler apparatus of simple construction.

What is claimed is:

1. In a surgical stapler apparatus the combination comprising
 a housing;
 a shaft movably mounted in said housing for relative longitudinal movement therein;
 an anvil mounted on a distal end of said shaft;
 an annular stapler pusher projecting axially from a distal end of said housing towards said anvil;

means for mounting an annular stapling cartridge on said housing in alignment with said pusher, said means including a sleeve slidably mounted on said housing for movement between an extended position and retracted position;

means for moving said shaft into said housing and said anvil towards said knife; and cam means between said housing and said sleeve for securing said sleeve relative to said housing during proximal movement of said anvil to a predetermined point relative to said housing, said cam means being positioned relative to said sleeve for movement relative to said housing in response to continued proximal movement of said anvil from said point whereby said anvil pushes said annular means relative to said pusher to expel staples from a stapling cartridge thereon for stapling of tissue between said anvil and a cartridge on said housing.

2. An apparatus as set forth in claim 1 wherein said shaft has a cam surface at an intermediate location within said housing and said cam means includes at least one ball mounted in said housing for radial movement during passage of said cam surface thereby.

3. An apparatus as set forth in claim 1 wherein said housing includes a pair of coaxial sections telescopically fitted into each other and which further includes a spring between one of said housing sections and said sleeve for biasing said sleeve into said extended portion.

4. An apparatus as set forth in claim 3 wherein the other of said housing sections includes a conical exterior surface and said sleeve has a conical interior surface for abutting said exterior surface in said extended position.

5. An apparatus as set forth in claim 1 which further comprises a pivotally mounted latch in said housing having a proximal end to abut said shaft to prevent proximal movement of said shaft from said point, cam means for pivoting said latch from said shaft and a cable extending from said cam means for moving said cam means to release said latch.

6. A flexible surgical stapler apparatus comprising
a housing;
a non-rotatable shaft slidably mounted in said housing;
a flexible axially rigid tube abutting said housing;
a cable within said tube and secured to said shaft for moving said shaft relative to said housing;
an anvil mounted on a distal end of said shaft;
an annular knife projecting from a distal end of said housing towards said anvil;
an annular staple pusher projecting from said distal end of said housing towards said anvil;
an annular stapling cartridge having a plurality of staples mounted in alignment with said pusher for stapling tissue disposed between said anvil and said cartridge;
a mounting ring concentric to and about said pusher mounting said cartridge thereon, said ring being movable between an extended position and a retracted position; and
means for securing said ring relative to said housing during movement of said anvil to a predetermined point spaced from said knife and for releasing said ring from securement with said housing in response to continued movement of said anvil towards said knife whereby said anvil pushes the tissue and said cartridge towards said pusher to expel said staples from said cartridge while pushing said staples through the tissue and against said anvil for clinching thereof.

7. An apparatus as set forth in claim 6 which further comprises a sleeve movably mounted about said housing with said ring at a distal end thereof and said means includes a plurality of balls mounted in said housing for radial movement, an annular cam surface on said sleeve in contact with said balls in said extended position of said mounting ring and an enlarged diameter portion on said shaft in contact with said balls in said extended position to secure said sleeve against axial movement.

8. An apparatus as set forth in claim 7 wherein said means includes a cam surface on said shaft at a distal end of said enlarged diameter portion to permit radial inward movement of said balls during movement of said can surface thereby to simultaneously release said sleeve for axail movement relative to said housing.

9. An apparatus as set forth in claim 8 which further comprises a spring between said housing and said sleeve biasing said sleeve in a distal direction.

10. An apparatus as set forth in claim 8 wherein said housing includes a pair of coaxial sections telescopically fitted into each other and which further includes a spring between one of said housing sections and said sleeve for biasing said sleeve in a distal direction.

11. An apparatus is set forth in claim 6 which further comprises a releaseable lock means for preventing proximal movement of said shaft past a predetermined point.

12. An apparatus as set forth in claim 11 wherein said lock means includes a latch pivotally mounted in said housing to abut said shaft, cam means for pivoting said latch from said shaft and a cable extending from said cam means for moving said cam means to release said latch.

13. An apparatus as set forth in claim 6 which further comprises at least one spline on said housing receiving said spline to secure said shaft against rotation in said housing.

14. An apparatus as set forth in claim 6 which further comprises a sleeve movably mounted about said housing with said ring at a distal end thereof, said sleeve having an internal surface abutting an external conical surface of said housing in said extended position of said ring and a spring between said housing and said sleeve biasing said sleeve against said external surface.

15. An apparatus as set forth in claim 14 wherein said means includes at least one latch mounted in said housing for radial movement, a cam surface on said sleeve in contact with said latch in said extended position of said ring and an enlarged diameter portion on said shaft in contact with said latch in said extended position to secure said sleeve against axial movement.

16. An apparatus as set forth in claim 15 wherein said means includes a cam surface on said shaft at a distal end of said enlarged diameter portion to permit radial inward movement of said latch during movement of said cam surface thereby to simultaneously release said sleeve for axial movement relative to said housing.

17. An apparatus as set forth in claim 14 wherein said housing includes an annular shoulder abutting said tube and positioned for abutting of said sleeve thereon in said retracted position of said ring.

18. An apparatus as set forth in claim 14 wherein said sleeve has a plurality of radially disposed apertures for venting a space between said sleeve and said housing.

19. A surgical stapler apparatus comprising
a housing;

a shaft movably mounted in said housing for relative longitudinal movement therein, said shaft having a cam surface at an intermediate location within said housing;

an anvil mounted on a distal end of said shaft;

an annular knife projecting axially from a distal end of said housing towards said anvil;

an annular staple pusher projecting axially from said end of said housing towards said anvil and radially outside said knife;

annular means for mounting an annular stapling cartridge having a plurality of staples on said housing in alignment with said pusher, said means including a sleeve slidably mounted on said housing for movement between an extended position and retracted position;

means for moving said shaft into said housing and said anvil towards said knife; and cam means for securing said sleeve relative to said housing during movement of said anvil to a predetermined point spaced from said knife, said cam means being positioned relative to said cam surface and said sleeve for movement relative to said housing in response to continued proximal movement of said anvil towards said knife from said point whereby said anvil pushes said annular means relative to said pusher to expel staples from a stapling cartridge thereon for stapling of tissue between said anvil and a cartridge on said annular means.

20. An apparatus as set forth in claim 19 wherein said cam surface is a conical annular surface and said cam means includes a plurality of circumferentially spaced balls mounted in said housing for radial movement during passage of said cam surface thereby.

21. An apparatus as set forth in claim 19 wherein said housing includes a pair of coaxial sections telescopically fitted into each other and which further includes a spring between one of said housing sections and said sleeve for biasing said sleeve into said extended portion.

22. An apparatus as set forth in claim 21 wherein the other of said housing sections includes a conical exterior surface and said sleeve has a conical interior surface for abutting said exterior surface in said extended position.

23. An apparatus as set forth in claim 19 wherein said annular means includes a cartridge mounting ring secured to and extending from said sleeve concentrically about said pusher and said knife.

24. An apparatus as set forth in claim 23 wherein said pusher is an annular ring having at least one annular row of fingers for pushing a row of staples from a cartridge mounted on said ring.

25. An apparatus as set forth in claim 19 wherein said pusher is an annular ring having at least one annular row of fingers for pushing a row of staples from a cartridge mounted on said annuluar means.

26. An apparatus as set forth in claim 19 wherein said means for moving said shaft is a flexible cable secured to a proximal end of said shaft.

27. An apparatus as set forth in claim 19 which further comprises a releaseable lock means for preventing proximal movement of said shaft past a certain point.

28. An apparatus as set forth in claim 27 wherein said lock means includes a pivotally mounted latch in said housing having a proximal end to abut said shaft, cam means for pivoting said latch from said shaft and a cable extending from said cam means for moving said cam means to release said latch.

29. An apparatus as set forth in claim 19 which further comprises at least one groove in said shaft and at least one spline on said housing receiving said spline to secure said shaft against rotation in said housing.

* * * * *

UNITED STATES PATENT AND TRADEMARK OFFICE
CERTIFICATE OF CORRECTION

PATENT NO. : 4,776,506
DATED : October 11, 1988
INVENTOR(S) : DAVID T. GREEN

It is certified that error appears in the above-identified patent and that said Letters Patent is hereby corrected as shown below:

```
Column 1, line 45 "stapler" should be -staple-
Column 2, line 6  "of" should be -into-
Column 5, line 43 "additio" should be -addition-
Column 6, line 50 "also," should be -also-
Column 6, line 67 "stapler" should be -staple-
Column 8, line 17 "axail" should be -axial-
```

Signed and Sealed this

Fourth Day of April, 1989

Attest:

DONALD J. QUIGG

*Attesting Officer*      *Commissioner of Patents and Trademarks*